(12) United States Patent
Spencer et al.

(10) Patent No.: US 11,568,541 B2
(45) Date of Patent: Jan. 31, 2023

(54) SYSTEM FOR HIGH PERFORMANCE, AI-BASED DAIRY HERD MANAGEMENT AND DISEASE DETECTION

(71) Applicant: EIO Diagnostics, Inc., Point Roberts, WA (US)

(72) Inventors: Cory Spencer, Duncan (CA); Damir Wallener, Duncan (CA); Jeff Sember, Vancouver (CA)

(73) Assignee: EIO DIAGNOSTICS, INC., Point Roberts, WA (US)

( * ) Notice: Subject to any disclaimer, the term of this patent is extended or adjusted under 35 U.S.C. 154(b) by 147 days.

(21) Appl. No.: 17/191,784

(22) Filed: Mar. 4, 2021

(65) Prior Publication Data

US 2021/0192736 A1 Jun. 24, 2021

Related U.S. Application Data

(62) Division of application No. 16/108,178, filed on Aug. 22, 2018, now Pat. No. 10,964,019.

(51) Int. Cl.
*G06T 7/00* (2017.01)
*A61B 5/11* (2006.01)
(Continued)

(52) U.S. Cl.
CPC ............ *G06T 7/0014* (2013.01); *A01J 5/007* (2013.01); *A61B 5/1118* (2013.01); *G06N 5/046* (2013.01);
(Continued)

(58) Field of Classification Search
CPC ....... G06F 19/30; G06F 15/18; A01K 27/009; A01K 5/0275; A01K 5/05; G06T 7/0014; G06T 7/11; G06T 7/187; G06T 3/40; G06T 7/70; A61B 5/1118; G06N 5/046; A01J 5/007
(Continued)

(56) References Cited

U.S. PATENT DOCUMENTS

2018/0082016 A1* 3/2018 Moshier ............... A01K 11/006
2018/0206448 A1* 7/2018 Madhusudan ....... A01K 5/0275

* cited by examiner

*Primary Examiner* — Phuoc H Doan
(74) *Attorney, Agent, or Firm* — Gearhart Law LLC; David Postolski

(57) ABSTRACT

Systems and methods for detecting udder disease based on machine learning methods and complementary supporting techniques are presented. Included are methods for assembling time sequences of images of each animal of a herd or set for subsequent use in per-animal image analysis for disease detection. Methods presented also include image pre-processing methods used prior to image analysis, resulting in contrast and resolution optimization such as appropriate image intensity level adjustment and resolution downsampling for more rapid and more accurate disease detection. Combinatorial techniques for compositing whole-udder images or udder-quarter images from partial images captures are described. Methods are provided for power usage optimization in regard to computing resources used in the computing-intensive AI analysis methods. Location-based and animal history-based detection refinements are incorporated into described systems. Further presented are methods for multi-modal and multi-factor detection of udder disease, as well as methods for infection type classification.

10 Claims, 3 Drawing Sheets

(51) Int. Cl.
*G06T 7/11* (2017.01)
*G06T 7/187* (2017.01)
*G06T 3/40* (2006.01)
*G06N 5/04* (2006.01)
*A01J 5/007* (2006.01)
*G06T 7/70* (2017.01)
*G06N 20/00* (2019.01)

(52) U.S. Cl.
CPC .............. *G06N 20/00* (2019.01); *G06T 3/40* (2013.01); *G06T 7/11* (2017.01); *G06T 7/187* (2017.01); *G06T 7/70* (2017.01); *G06T 2207/10048* (2013.01)

(58) Field of Classification Search
USPC .............................. 382/128, 110; 340/573.3
See application file for complete search history.

SYSTEM FOR HIGH PERFORMANCE, AI-BASED DAIRY HERD MANAGEMENT AND DISEASE DETECTION

CROSS-REFERENCE TO RELATED APPLICATIONS SECTION

This application is a United States Non-Provisional patent application and Divisional of U.S. Non-Provisional patent application Ser. No. 16/108,178 filed on Aug. 22, 2018, the entire contents of which are hereby incorporated by reference in their entirety.

FIELD OF THE EMBODIMENTS

The present invention is generally related to animal husbandry and, in particular, to animal husbandry involving disease detection, artificial intelligence (AI), thermal imaging, and image processing.

BACKGROUND OF THE EMBODIMENTS

The health of the animals in a domestic herd affects their well-being, and can impact that of the consumers of products derived from the herd animals. Specific aspects of animal health, such as udder condition and the presence of udder disease (in the case of dairy animals), directly impact farm productivity, ultimately affecting the availability and cost of dairy-derived foods.

Significant advances have been made in recent years in the area of technology called artificial intelligence (AI), also known as machine learning, in regard to the expression and solution of complex, difficult-to-describe problems. Candidate problems typically involve large data sets having significant sample-to-sample variability and noise, and the solution may require the identification of one or more trends, or the extraction of one or more feature types, from the data.

For these reasons, effective, rapid animal condition assessment and early and reliable detection of disease is vitally important in animal farming operations of all scales. In addition, with the growth and increasing overall wealth of the human population, demands have increased for the production of high-value food by farms. Additionally, there are substantial benefits to be gained from innovations that lead to increased farm productivity.

Examples of related art are described below:

U.S. Pat. No. 7,277,744 generally describes a method for the detection of inflammation in animals using infrared thermography. The patent also provides a method for the detection of diseases or disorders that induce inflammation using infrared thermography. The present invention further provides a method for the detection of infections in animals using infrared thermography.

U.S. Pat. No. 7,399,220 generally describes a method and apparatus for measuring the physical characteristics of livestock animals such as cattle and hogs. The apparatus of the invention includes a plurality of strategically positioned cameras that are used to obtain data concerning volumetric, curvilinear (surface) and linear measurements of livestock animals such as cattle and hogs and the full carcasses thereof. In accordance with the method of the invention, the data is analyzed to provide information that substantially assists the commercial producer of livestock animals in producing a high-quality end-product for the consumer while adding profitability to the enterprise.

U.S. Pat. No. 8,789,494 generally describes an apparatus for monitoring a milking animal during milking of the animal. The apparatus includes a number of productivity sensors, each measuring at least one indicator of productivity of the animal. A number of temperature sensors, including at least two thermographic cameras, measure heat output from different processing areas of the milking animal. A processor receives the heat outputs and productivity indicators, and uses a combination of these to determine a condition of the milking animal. The condition is then indicated in real time at the monitoring apparatus.

U.S. Patent Publication No. 2005/0257748 generally describes a method and apparatus for measuring the physical characteristics of livestock animals such as cattle and hogs. The apparatus of the invention includes a plurality of strategically positioned cameras that are used to obtain data concerning volumetric, curvilinear (surface) and linear measurements of livestock animals such as cattle and hogs and the full carcasses thereof. In accordance with the method of the invention, the data is analyzed to provide information that substantially assists the commercial producer of livestock animals in producing a high-quality end-product for the consumer while adding profitability to the enterprise.

U.S. Patent Publication No. 2013/0319336 generally describes an apparatus for monitoring a milking animal during milking of the animal. The apparatus includes a number of productivity sensors, each measuring at least one indicator of productivity of the animal. A number of temperature sensors, including at least two thermographic cameras, measure heat output from different processing areas of the milking animal. A processor receives the heat outputs and productivity indicators, and uses a combination of these to determine a condition of the milking animal. The condition is then indicated in real time at the monitoring apparatus.

U.S. Patent Publication No. 2017/0006838 generally describes A system for locating the position of at least one animal within a predetermined region of space. The system includes at least one identification means configured to transmit at least one identification signal associated with said at least one animal; at least one locating means configured to generate at least one location signal associated with said at least one animal; and, a data processing system in communication with said at least one identification means and said at least one location means, configured to analyze said signals, said analyzed signals comprising the position within said predetermined region of space of said at least one animal as a function of time; wherein said data processing system is configured to integrate over time multiple readings from said at least one first animal to make a reliable estimation of said location of said animal within said predetermined region of space.

None of the art described above addresses all of the issues that the present invention does.

SUMMARY OF THE EMBODIMENTS

According to an aspect of the present invention, a method for automatically assembling sequences of images of udders of a set of dairy animals, with each animal identified and with each image having a timestamp, for use in detecting udder disease, is provided. The method includes identifying an identity of each animal in the set of dairy animals, using one or more sensors, wherein each animal is an animal having an udder. The method further includes imaging all or a portion of the udder of each animal at a first time, creating one or more first images with an image capture time recorded as the timestamp, assigning the one or more images and timestamps to each identified animal, identifying an identity of another animal, using one or more sensors, and sorting the images by animal and by capture time, for use in machine learning or change detection analysis against one or more reference images for the purpose of detecting udder disease.

It is an object of the present invention to provide the method for automatically assembling sequences of images of udders of a set of dairy animals, with each animal identified and with each image having a timestamp, for use in detecting udder disease, wherein the identifying further includes scanning one or more tags on the animal.

It is an object of the present invention to provide the method for automatically assembling sequences of images of udders of a set of dairy animals, with each animal identified and with each image having a timestamp, for use in detecting udder disease, wherein the one or more tags are RFID tags.

It is an object of the present invention to provide the method for automatically assembling sequences of images of udders of a set of dairy animals, with each animal identified and with each image having a timestamp, for use in detecting udder disease, wherein the imaging the one or more udders at a first time and the imaging the one or more udders at a second time are performed using one or more thermal sensors.

It is an object of the present invention to provide the method for automatically assembling sequences of images of udders of a set of dairy animals, with each animal identified and with each image having a timestamp, for use in detecting udder disease, wherein the images are thermal images.

It is an object of the present invention to provide the method for automatically assembling sequences of images of udders of a set of dairy animals, with each animal identified and with each image having a timestamp, for use in detecting udder disease, wherein the analyzing further includes isolating an udder from within each image.

It is an object of the present invention to provide the method for automatically assembling sequences of images of udders of a set of dairy animals, with each animal identified and with each image having a timestamp, for use in detecting udder disease, wherein the method further includes scanning one or more sensors on or within the animal to determine any physical activity of the animal.

It is an object of the present invention to provide the method for automatically assembling sequences of images of udders of a set of dairy animals, with each animal identified and with each image having a timestamp, for use in detecting udder disease, wherein the one or more sensors on or within the animal includes a GPS sensor.

It is an object of the present invention to provide the method for automatically assembling sequences of images of udders of a set of dairy animals, with each animal identified and with each image having a timestamp, for use in detecting udder disease, wherein the analyzing further includes analyzing any changes between the one or more first images and the one or more second images in view of the physical activity of the animal.

It is an object of the present invention to provide the method for automatically assembling sequences of images of udders of a set of dairy animals, with each animal identified and with each image having a timestamp, for use in detecting udder disease, wherein the animal is a cow.

It is an object of the present invention to provide the method for automatically assembling sequences of images of udders of a set of dairy animals, with each animal identified and with each image having a timestamp, for use in detecting udder disease, wherein the method further includes determining an activity level of the animal.

It is an object of the present invention to provide the method for automatically assembling sequences of images of udders of a set of dairy animals, with each animal identified and with each image having a timestamp, for use in detecting udder disease, wherein the activity level is determined by analyzing movement of the animal.

It is an object of the present invention to provide the method for automatically assembling sequences of images of udders of a set of dairy animals, with each animal identified and with each image having a timestamp, for use in detecting udder disease, wherein the movement of the animal is determined using one or more sensors.

It is an object of the present invention to provide the method for automatically assembling sequences of images of udders of a set of dairy animals, with each animal identified and with each image having a timestamp, for use in detecting udder disease, wherein the method further includes identifying one or more images for further use in presenting or studying a time progression of udder disease within a given animal, wherein the one or more images are detected as containing possible diseased areas.

It is an object of the present invention to provide the method for automatically assembling sequences of images of udders of a set of dairy animals, with each animal identified and with each image having a timestamp, for use in detecting udder disease, wherein the method further includes performing adjustments to individual pixel values of potential regions of interest of the images within specified maxima and minima and according to a specified scaling function applicable to original pixel values, to increase image contrast for better detection of a diseased area.

It is an object of the present invention to provide the method for automatically assembling sequences of images of udders of a set of dairy animals, with each animal identified and with each image having a timestamp, for use in detecting udder disease, wherein the method further includes combining multiple partial image captures of a given animal udder through geometric transformations to form a complete or more nearly complete udder image for subsequent use in image analysis for disease detection.

According to another aspect of the present invention, a method for producing an approximately complete image of an animal's udder from partial images is provided. The method includes capturing multiple images of the udder, from a variety of angles and distances, mathematically combining the images to form one larger image covering the approximate entirety of the udder, employing geometric transformation of the resulting image to area-equalize all parts of the udder, wherein every subsection of the image is a correct size relative to the rest of the udder, and normalizing sensor values for each image combined into the larger image so that image pre-processing can be correctly executed on regions of a resulting image.

According to yet another aspect of the present invention, a method for locating udder disease within individual udder quarters or halves, in which udder quarters or halves are identified based on knowledge of udder biology for an animal species is provided. The method includes annotating an image for each udder quarter or udder half, saving an image annotation in an ancillary database, drawing one or more overlays on the image to visually identify one or more udder sections, associating each udder quarter or udder half with one or more biological data measurements from a particular part of an udder, and performing disease detection localized to each udder quarter or udder half using a resultant image and image analysis.

According to a further aspect of the present invention, a method for reducing a resolution of images to expedite processing for machine learning applications such as disease detection is provided. The method includes determining a distance between a sensor and a target, determining a physical area corresponding to a coverage by one sensor pixel, thereby calculating a clustering factor as a ratio or other function of the physical area per pixel, and applying a downsampling algorithm to an input image based on a clustering factor to produce a second image, the second image being of reduced resolution for use as input to a machine learning system.

DESCRIPTION OF THE PREFERRED EMBODIMENTS

Figure 1:
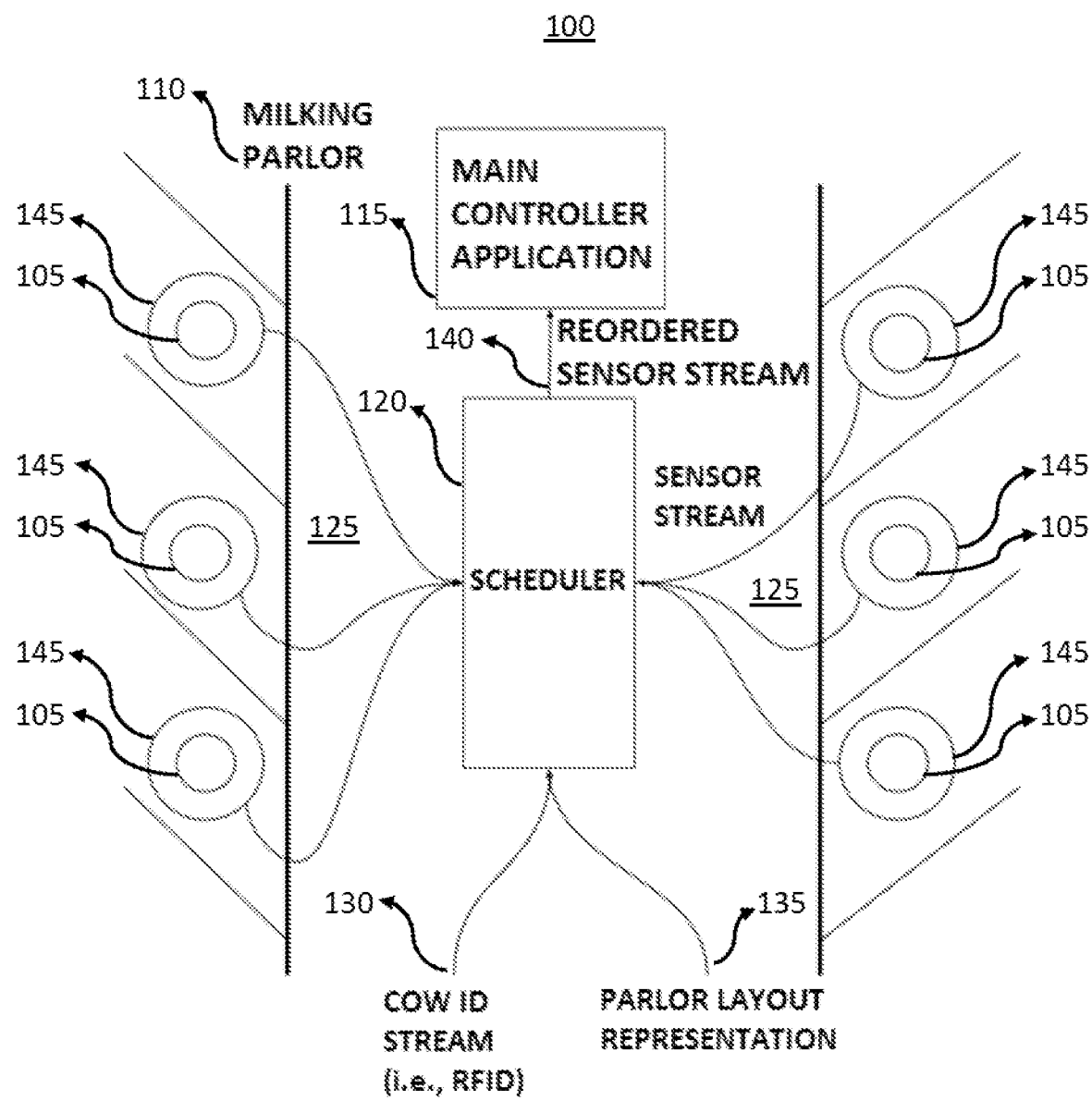
FIG. 1 shows an illustration of a milking parlor system layout, according to an embodiment of the present invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Referring now to FIG. 1, a diagram of a milking parlor system layout 100 for a milking parlor 110 is illustratively depicted, in accordance with an embodiment of the present invention.

A modern large dairy farm may have tens or hundreds of milk-producing animals 105, and may utilize several robot milkers (machines designed to milk the milk-producing animals). For example, a 150 herd dairy farm may have three milking robots. A given cow 105 on such a farm can go to any milking robot for a milking session.

Early detection of disease onset as well as the progression of udder disease is of high important to the health of the animals. Therefore, udder inspection and analysis for any given cow is desired and is a result of collating results from multiple sensors or sensor sets, each sensor or sensor set being associated and co-located at a particular station, such as a milking stall, potentially with a given milking robot for a given milking and data capture session.

Time Series Assembly

One objective in the preparatory stage of the analysis performed in the present invention is to rapidly and reliably assemble a time series of data sets for each animal 105. According to an embodiment, the data is aggregated coherently from multiple stations. This allows for temporal analytic techniques, such as change detection, as well as for observation of the case histories of specific animals, potentially through onset as well as at clinical or treatment stages. It also facilitates comparisons of results from disparate sensors, since multiple sensor sets can be tested ad locum against known-condition reference animals or with simulated inputs. According to an embodiment, as each cow 105 enters a station 145, it is first identified by some means, such as, e.g., recognition of an RFID tag 130 or unique tattoo or marking. The local sensor(s) for that station sends a stream 125 of data to a scheduler unit 120. The scheduler uses the cow ID stream and parlor layout map or other representation 135 to reorder the image stream from the sensors, forming a reordered sensor stream 140. The reordered sensor stream 140 is then sent to a main controller application 115. This technique produces a sequential data set per animal and is illustrated in FIG. 1.

While the above description is largely for the case of cows at milking stations, the present system for/method of disease detection is not limited to milking stations. The present system and/or method may be used for the analyzation of any suitable animal, while maintaining the spirit of the present invention. For example, according to an embodiment, the thermal cameras that supply data to the processing computers can alternately be located at feeding stations or at any other deployment location where a view of the animal's udder is available.

Image Pre-Processing for Detection Enhancement:

In general, high contrast images are assistive to feature extraction by AI methods and by other feature extraction techniques, and can also make image features easier for human viewers to see, as compared to low contrast images.

The working environment for the sensors of the present detection system can have wide range of recordable temperatures. Thermal sensors have a limited dynamic range for covering the possible temperatures to be measured, and the post-capture digital output of the sensor pixels is also limited to a specific value range per pixel. By defining a range of temperatures of interest and taking certain other steps after image capture, such as, e.g., adjustment of tonal curves, it is possible to maximize the available dynamic range of the output in post-capture image processing to produce high contrast images, prior to performing the ultimate AI disease detection work.

Within the present invention, according to an embodiment, a method of doing this pre-processing is to use the following steps:

1. Identify an initial region of interest (ROI) in the image;
2. Calculate a central Temperature Score for the ROI, such as, e.g., an average of all the values of pixels in the ROI; and
3. Determine, using the software, upper and lower limits of interest based on maximum and minimum individual pixel values from within the ROI. According to an embodiment, for an entire image, pixel values below the minimum are set to 0, and values above the maximum are set to 255. Intermediate values are scaled either linearly or using an applied tonal curve.

According to an embodiment, other image processing techniques may also be implements, while maintaining the spirit of the present invention. According to an embodiment, image processing techniques may include, e.g.:

Resolution mapping: The sensor has a natural resolution. When viewing an object from a set distance, each pixel can be imagined to cover a specific physical area on the target. For example, a 320×320 pixel array at half a meter distance from an object is approximately using one pixel to cover one square millimeter of surface area. In this application, the goal is to identify symptoms related to biological phenomena, such as, e.g., fever/body temperature. These objects manifest as objects larger than a single pixel—i.e., following the example above, a patch of skin with elevated temperature would always be greater than 1 square millimeter, due to the thermal diffusion of living material. This means more detail is being captured than is warranted by the object under inspection. Machine learning systems, particularly those dealing with vision, have performance (speed and accuracy) highly correlated with the number of pixels in the image. According to an embodiment, the present invention takes advantage of the disparity between the sensor resolution and the resolution of the biological phenomena by employing clustering algorithms to "downsample" the raw image to a lower resolution. This lower resolution image is then used to train the artificial intelligence inference engine (a "neural network" in common usage). According to an embodiment, the steps may include:

a. Determining distance between sensor and target by any practical method, such as requiring a set distance, or measuring a set distance on installation, or dynamically determining distance between sensor and target by use of ratio of sizes of known objects (i.e., an udder should be "this big", this one is "that big", divide to find the scaling factor).

b. Determining the physical area corresponding to coverage by one sensor pixel, and using the ratio, calculate the clustering factor.

c. Applying a down-sampling algorithm to the input image based on the clustering factor, use this image (instead of the raw/original image) as input to the machine learning training system.

This results in an image that visually looks like a low resolution version of the original image. This can also be combined with upper and lower thresholds on pixel values, as described earlier, to increase the visual contrast in the image. The thresholding can occur before or after the clustering. This can also be combined with grouping sensor pixel values into ranges, prior or after, the clustering. Each range is associated with a different color, or gray scale value. For example, if the pixel values can take on values between 1 and 100, clustering could create ranges 0-9, 10-11, 40-49, etc. Then each pixel has its original value mapped to a new value corresponding to which range it is in. This process is sometimes called "binning", and results in an image that appears "posterized". That is, there are fewer color/gray gradients, and more solid blocks of color/gray.

"Bubble wrap": Using images to train a vision-based machine learning system requires annotation of the images with "labels". Successful training is dependent on accurate, specific labelling. With large datasets, it is important to automate the labeling of training images, otherwise the task quickly becomes intractable. To facilitate training of the artificial intelligence inference engine, the image pre-processor performs the following steps:

a. Accepting an image as input (can be either unaltered, or enhanced using one of the methods described above.

b. Using a definition of "anomaly", identifying regions of interest in the image that meet the definition of anomaly.

c. For each anomaly, creating a visual "tag" on top of or tightly around the anomaly. For example, on a gray scale image, the current embodiment overlays a red circle, sized to correspond to the size of the anomaly.

According to an embodiment, a further enhancement is to allow the definition of "anomaly" be based on the characteristics of the image under consideration. That is, the image is mathematically analyzed to determine the range and distribution of sensor pixel values, a definition of "anomaly" is programmatically defined using this analysis, and applied to "tag" the image with the visual indicator. The modified/tagged image then becomes part of the machine learning training dataset.

Udder Stitching:

According to an embodiment, for optimum results, the entire surface of the udder should be imaged. Depending on the relative positions of the animal and the sensor, this may not be possible to do with just one image. If the sensor is mounted on a movable platform—for example, on the head of a milking robot arm, or at the end of a selfie stick—it can image the entire udder through a succession of images. This sequence of images can then be stitched together to form one complete image of the udder.

According to an embodiment, udder stitching may include the following steps:

i. Capturing multiple images of the udder, from a variety of angles/distances.

ii. Mathematically combining the images to form one larger image covering the entirety of the udder.

iii. Employing geometric transformation of the resulting image to area-equalize all parts of the imaged udder. That is, transforming, as necessary, so that every subsection of the image is the correct size relative to the rest of the udder.

iv. Normalizing sensor values for each image combined into the larger image so that image pre-processing, as defined earlier in this document, can be correctly executed on regions of the resulting image that were originally covered by different images.

Udder Quartering and Halving:

Biologically, for many considerations, an udder can be thought of as a multi-chamber organ, where the various chambers are relatively independent, biologically. A cow has four such chambers while a goat has two. Some udder illnesses manifest in only one "chamber" of the udder. For biological events that manifest in individual chamber, we want to perform analysis on the captured udder images by regions that correspond to those chambers. With the capture of a good, normalized photo of the udder, distinctly showing 4 quarters, the present system is capable of plotting/predicting a series of points that divide the udder up into each quarter with sufficient training. This enables the users of the present system to predict mastitis on a per quarter basis as opposed to on the udder as a whole in the case of the fixed sensor. According to an embodiment, this may be performed using the present invention using the following methods.

a) Programmatically identifying the quarters/halves using knowledge of udder biology for that species (for example, a cow will have four udder sections, each with its own teat, and rear quarters will have a different shape/size than front quarters, etc.).

b) Programmatically creating labels and "annotate" the image for each quarter/halve, saving that information is an ancillary file/database, and possibly drawing overlays on the image itself to visually identify the udder sections.

c) Associating each quarter/halve with the biological data measurements from that part of the udder (i.e., per-teat Somatic Cell Counts or bacterial culturing results).

d) For all of the image pre-processing techniques above, applying them per-quarter/halve rather than across the entire udder.

Machine learning training can now be done on either the entire udder, or on the udder, by sections. It can also be done both, and a supervisory algorithm can choose between them, or combine them.

Time-Based Compression and History Utilization:

In video processing, a common technique for compressing data is to through the use of key frames plus a record of differences between other images (known as "deltas") and the key frame, so that a given image can be reconstructed as the sum of the key frame and the appropriate delta(s). This is particularly effective in a time series, where successive frames tend to have substantial similarity to previous ones. This can provide significant compression of data streams.

The present invention deals not just with instantaneous images of cow udders, but with the history of the udders. Therefore, because analysis has to happen in real time, the present system benefits from a similar way of similarly "compressing" udder history.

Analysis at any given moment is then done by looking at the current complete image, along with a compressed time history of the same cow's udder going back some number of instances. The present system accomplishes this by first designating a given image at a specific point in time, such as a first image captured, as a key frame. That image is stored in its entirety. For the next image, only deltas from the last key frame need be stored. Subsequent images are then compared against the last key frame, with deltas being serialized.

Over time, what is created is essentially a time series history of anomalies, instead of full uncompressed images of the udder, but full images can be constructed as needed. According to the analysis of the present invention, the same spot on the current image can be viewed that previously showed an anomaly relative to the key frame, and it can then be determined whether it forms a trend with the time history.

Power-Optimized Infection Detection:

The present system design presents several opportunities for minimizing the use of electrical energy and for optimizing use of available computing resources ("computing power").

Typically, a computing system for use in AI computations consists of multiple CPU cores plus associated resources of addressable volatile memory and longer term data storage. The problem that is addressed with the present invention typically can be broken down into at least the two following sub-problems:

1. Finding of an udder within an image; and
2. Computation of the presence or absence of a diseased area or other anomaly of concern within the udder recognized within sub-problem 1.

Out of this sub-problem definition, the following power optimizations have been arrived at within the present invention. According to an embodiment, a subset of available computing resources is defined as "Set A" and is assigned to the task of solving problem 1. "Set B" corresponds to a different, possibly larger, subset of computational resources. For example, the computing platform may consist of a multi-core device. Set A may be configured to use only one of the CPU cores. Set B may use all of the cores. This can be extended to more than two compute sets, depending on the hardware platform and needs.

As a practical example, there may be multiple machine learning inference engines. One machine (Machine 1) is trained to detect udders, the second machine (Machine 2) is trained, given a confirmed udder input image, to perform a diagnostic analysis on the image. A third machine/inference engine (Machine 3) may be trained to perform a diagnostic on an image from an entirely different sensor, where the udder is identified by the first inference engine. In this scenario, there is no reason to run Machine 2 or Machine 3 until Machine 1 actually detects an udder. This saves power.

According to an embodiment, "Set B" may also refer to an increase in operating frequency of the cores, increased access to memory, access to networking services, access to different storage devices, etc.

Set A operates in an "on" or actively processing state during any time that image data is available for processing. Set B is only turned on and applied to solving problem 2 when udder(s) have been detected via processing by Set A as the solution of problem 1.

In the example given above with two base problems and two sets of computing resources, Set A is always on and handling new images as received, and Set B is turned on only on demand. It is noted, however, that other variants are possible and contemplated within the present invention, for managing available computing resources in view of energy consumption and other constraints such as, e.g., minimum processing time. For example, the set of resources applied to solve a given detection problem may be reduced if current results are being obtained at least quickly enough to satisfy the rate that images are being received by the system as dairy animals are milked in the milking system. It is also noted that, according to various embodiments, resources such as CPU cores and memory may also be re-allocated between resource sets subject to the performance and computing demands of recent diagnostic results.

Figure 2:
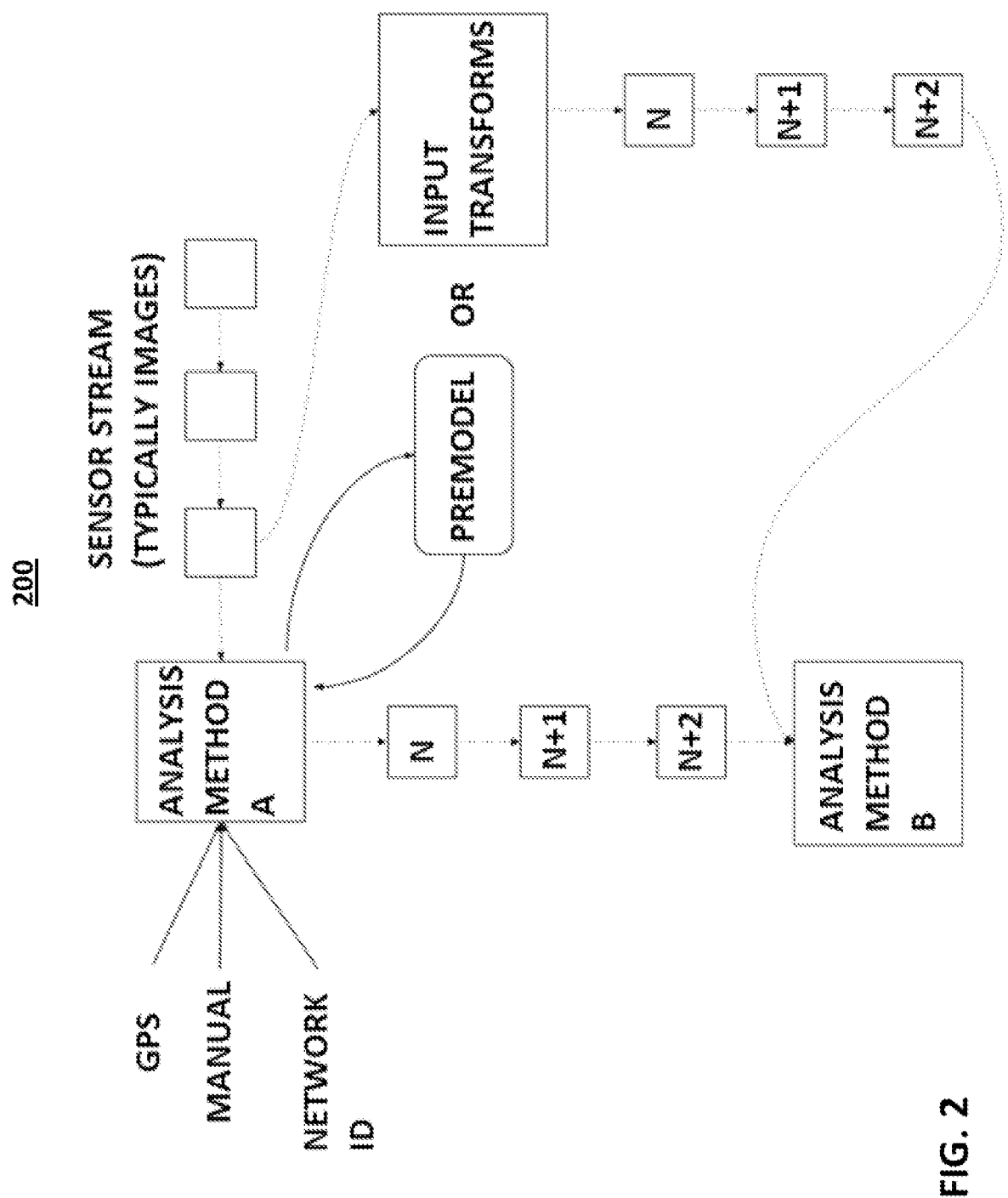
FIG. 2 shows a diagram of location-enabled modeling, according to an embodiment of the present invention.

Referring now to FIG. 2, a diagram 200 of location-enabled modeling is illustratively depicted, in accordance with an embodiment of the present invention.

Location-Based and Animal History-Based Detection Refinement:

Animal characteristics are often dependent on how the animal is raised. This tends to be location specific. For example, it has been found that, in North American farms, cows are relatively sedentary; they typically don't walk around much, and get fed large amounts of grain at fixed feeding station locations. However, on farms in New Zealand, cows walk around frequently, and are mostly pasture-fed. This produces udders that are different in shape, as well as other characteristics that are distinct from cows raised elsewhere or with different activity histories.

When trying to identify udders, it is useful, then, to understand what kind of animals are being viewed and, especially, what their activity history has been. For machine learning applications, this is important because location awareness can enable representative models and reference images to use for training the present AI system to be selected more closely.

Within the present invention, representative reference images can be selected for use in the present AI system based on known farm locations, or from locations obtained by GPS or other location-sensing technologies. According to an embodiment, the location can be determined using GPS, manually inputting the location, network ID, and/or any other suitable method of determining location. Farm location and other "metadata" for each animal can be automatically referenced and retrieved from a database via unique animal identifiers such as, e.g., RFID tags.

According to an embodiment, the system enables knowledge to be obtained of the degree of physical activity of a given animal from the location history of that animal from serialized data obtained from location tracking devices such as, e.g., a GPS receiver attached to the animal. According to an embodiment, the position of the animal is determined at time N, N+1, N+2, ..., N+n. That data can be filtered by data such as maximum velocity to remove inapplicable motion data such as the animal having been transported by truck at roadway speed, rather than from the animal's own locomotion. The information as to the degree of activity of the animal thusly obtained can then be used to select reference images to be used for training our AI system.

Detection Enhancement with Multifactor Diagnostics and Multi-Modal Sensing:

According to an embodiment, the present system is capable of using data input from a multitude of sensor types and wavelengths to enhance and refine disease detection capabilities. Such multi-modal data can be combined, compared, or used independently during analysis for disease detection. For example, images from visual and thermal wavelength sensors may be utilized in the same diagnostic run; coupled visual and thermal data sets per animal can be compared with reference data set coupled pairs of the same modalities. In addition, features found in one modality or spectral range can be cross-correlated in another.

Figure 3:
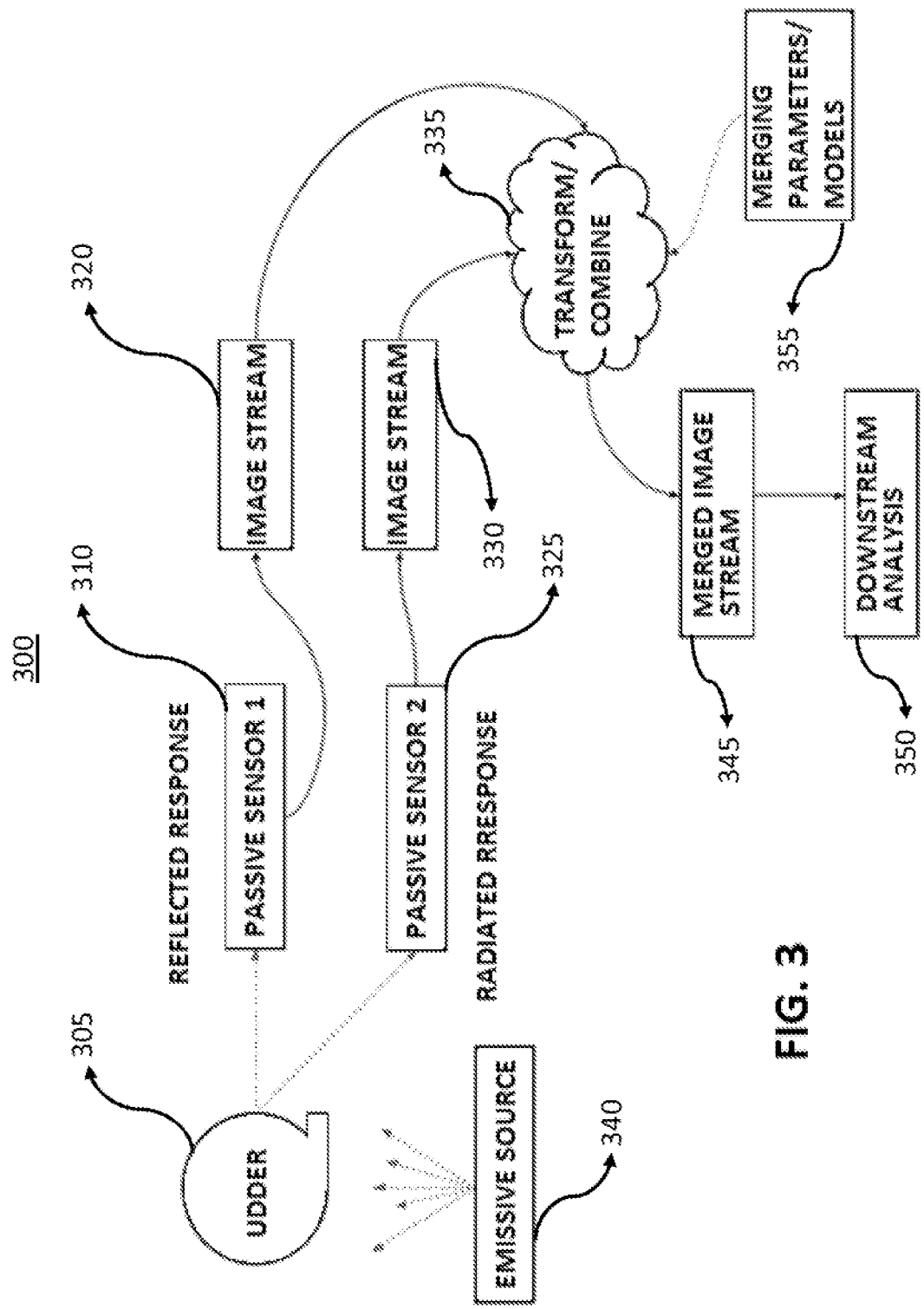
FIG. 3 shows an illustration of fusion of multi-sensor outputs, according to an embodiment of the present invention.

Referring now to FIG. 3, a diagram 300 showing an illustration of the fusion of multi-sensor outputs is illustratively depicted, in accordance with an embodiment of the present invention.

As an illustration of how multiple images can be used to train a more capable machine learning system, consider the following scenario, limited to two images for the sake of conciseness. A first image stream 315 carrying an image of an udder 305 is provided by a first passive sensor 210 (e.g., a long wave infrared sensor). This provides a "temperature map" of the surface of the udder 305. A second image stream 330 carrying a second image is provided by a second passive sensor 325 (e.g., a terahertz sensor). This provides a structural/density map of the top few millimeters of tissue. That is, the grayscale image intensity is proportional to the density of the biological material at the physical location corresponding to the sensor pixel.

Each of these images can be treated independently, undergo the types of processing and pre-processing described elsewhere in this document, and can go into separate machine learning training sets. That is, the infrared images train one machine, the terahertz images train a second machine. Then a supervisory algorithm can combine 335 the outputs of both systems to make a decision or provide a notification to the user.

Alternately, the information in both images can be used to create one enhanced image, and only one machine learning system needs to be trained. For example, the infrared sensor 310 shows a high resolution heat map of the udder 305 surface. The terahertz sensor 325 provides a map of the vascular structure just under the surface of the udder 305. Enhancing the infrared image with the terahertz image gives the ability to "label" which temperature anomalies correspond to a biological feature, such as vascularity. This gives a means of identifying when an infection, if detected, is related to Gram-positive or Gram-negative bacteria.

In this scenario, the infrared image is annotated with the terahertz information, and the machine learning proceeds with one training dataset instead of two. This is a much faster training path. It also eliminates the need for a supervisory algorithm to interpret/combine the outputs of two inference engines, because the machine learning output is now just one inference engine. Apart from training speed improvements, this also provides runtime performance improvements.

According to an embodiment, an emissive source 340 can be used with a passive sensor 310, 325 to identify additional features. According to an embodiment, the passive sensor 310, 315 may receive a reflected and/or radiated response. For example, a low power THz source can be radiated at a target, while being monitored by a LWIR (long wave infrared) sensor. The image formed by the sensor will be different from the image formed when operating in passive/non-emissive mode. The images can thus be combined 335 into a merged image stream 345, using merging parameters/models 355, to glean more information using downstream analysis 350 than would otherwise be discoverable. For example, a temperature anomaly on its own may indicate the possible presence of a diseased area. However, a temperature anomaly in the same location as a physical anomaly located by the emissive detection would confirm a physically damaged and infected region. In other cases, the degree of visibility of a diseased area can vary during the stages of progression and remission of the disease and healing of the damaged area.

According to an embodiment, thermal imaging may provide the earliest indication of inflammation caused by reaction to disease but, at later stages, irritated surface areas viewable at visible wavelengths can be useful indicators of the state of diseased areas.

The availability of multispectral imaging leads to other possibilities for the presentation of the results of the diagnostic analysis. Once analysis based on thermal imaging data detects the presence of a diseased region, if visible-spectrum imaging data (conventional photographic image) is available for an overlapping area with the diseased region and the spatial relationship between the thermal and visible areas is known, via calibration of coverage areas of the corresponding sensors or by other means such as coincident sensor coverage, then the detected diseased area can then be shown in a visible spectrum image presentation as a highlighted area so that a human viewer can more easily inspect the location of the diseased area by looking at the conventional visible image. According to an embodiment, said highlighting may consist of a visible box or other polygon enclosing the diseased area, or by contrast enhancement or colored shading of the diseased area of concern, or by other visible means representative of the location of the diseased area.

Automatic Classification of Infections:

One of the most common categorizations of infections is as Gram-positive infections. Gram-positive originates from the staining technique devised by Hans Christian Gram, circa 1884. Based on the techniques described above and the following special methods, the present invention is able to use sensors and image analysis to detect the difference between Gram-positive infections and other types of infections. This is important because infections caused by Gram-positive bacteria generally require different treatment than those caused by commensal or Gram-negative bacteria. This is important because it has a direct impact on treatment costs (i.e. economic benefit for the farmer). Gram-positive infections present different manifestations than other types of infections when imaged by (for example) longwave infrared. The differences are observable in both static images (different clustering/location of the hot spots) and in time series images (over a sequence of X days, the pattern demonstrated as the illness grows is different between Gram-positive and the other types).

This is not limited to Gram-positive. It is possible to identify further granularities between bacterial types, and it is even possible, at least in some cases, to actually identify the specific pathogen.

The way the machine learning engine is trained is essentially as follows:

i. Collect time series images on the same animal for X days/milking (generally need at least three images at consistent intervals).

ii. Collect biological testing data corresponding to the image (for example, somatic cell counts, electroconductivity readings, bacteriological culturing results) across the same time interval (doesn't have to be 1:1, or even necessarily overlapping).

iii. Annotate the biological data into/onto the sensor image(s).

iv. Structure the training method to utilize time series data (i.e., not just looking for something in an image, but looking at changes between sequences of images).

v. Train the machine.

vi. Validate by testing predictive capability against live animals, with confirmation by (for example) somatic cell count or bacteriological culturing tests.

vii. Repeat, refine training and analysis, if needed,

It is further noted that the present invention has applications in infection diagnosis for subjects beyond dairy animals, such as for humans and other species.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A method for locating an udder disease in an udder of an animal, the method comprising:
    utilizing one or more sensors mounted on a movable platform to identify an animal based on a unique identifier associated with the animal;
    capturing, via the one or more sensors mounted on the movable platform, a succession of images of an udder of the animal at varying angles and distances in relation to the udder of the animal;
    combining the succession of images of the udder of the animal into a complete image of the udder of the animal;
    annotating the complete image of the udder of the animal for one or more udder quarters or one or more udder halves;
    saving an image annotation in an ancillary database;
    drawing one or more overlays on the complete image of the udder of the animal to visually identify one or more udder sections;
    associating the one or more udder quarters or the one or more udder halves of the udder with one or more biological data measurements from a particular part of the udder; and
    performing disease detection localized to the one or more udder quarters or the one or more udder halves using a resultant image and image analysis.

2. The method of claim 1, wherein the combining of the succession of images of the udder of the animal into the complete image of the udder of the animal comprises:
    mathematically combining the succession of images of the udder of the animal into the complete image of the udder of the animal; and
    employing a geometric transformation of the complete image of the udder of the animal to area-equalize all parts of the udder of the animal.

3. The method of claim 1, wherein the animal is selected from the group consisting of: a cow and a goat.

4. The method of claim 1, wherein the annotating of the complete image of the udder of the animal for the one or more udder quarters or the one or more udder halves comprises:
    programmatically identifying the one or more udder quarters or the one or more udder halves using knowledge of udder biology for a species of the animal;
    programmatically creating labels to annotate the complete image of the udder of the animal for the one or more udder quarters or the one or more udder halves; and
    associating the one or more udder quarters or the one or more udder halves with biological data measurements from an associated part of the udder.

5. The method of claim 1, wherein the ancillary database comprises datasets containing clinically healthy images of an udder quarter of the animal, clinically healthy images of an udder half of the animal, mastitic images of the udder quarter of the animal, and mastitic images of the udder half of the animal.

6. The method of claim 5, further comprising:
    comparing the complete image of the udder of the animal to the datasets in the ancillary database to identify whether the one or more udder quarters in the complete image are more similar to the clinically healthy images of the udder quarter of the udder of the animal or the mastitic images of the udder quarter of the udder of the animal or identify whether the one or more udder halves in the complete image are more similar to the clinically healthy images of the udder half of the udder of the animal or the mastitic images of the udder half of the udder of the animal.

7. The method of claim 6, further comprising:
    identifying a diagnosis based on the comparison.

8. The method of claim 1, wherein the one or more sensors comprises a singular sensor that is configured to capture the succession of the images over a time period.

9. The method of claim 1, wherein the one or more sensors comprises a set of sensors.

10. The method of claim 1, wherein the unique identifier is selected from the group consisting of: an Radio-frequency identification (RFID) tag, a tattoo, and a marking.

* * * * *